United States Patent [19]
Belman et al.

[11] Patent Number: 4,981,295
[45] Date of Patent: Jan. 1, 1991

[54] RESPIRATORY TRAINING USING FEEDBACK

[75] Inventors: Michael J. Belman, West Covina; Brian Tiep, Monrovia, both of Calif.

[73] Assignee: City of Hope, Duarte, Calif.

[21] Appl. No.: 48,565

[22] Filed: May 11, 1987

[51] Int. Cl.⁵ ............................................. A63B 23/00
[52] U.S. Cl. ........................................ 272/99; 128/725
[58] Field of Search ................... 272/99; 128/207.16, 128/725, 720

[56] References Cited

U.S. PATENT DOCUMENTS

| | | | |
|---|---|---|---|
| 3,991,304 | 11/1976 | Hillsman | 128/725 X |
| 4,025,070 | 5/1977 | McGill et al. | 272/99 |
| 4,221,381 | 9/1980 | Ericson | 272/99 |
| 4,444,201 | 4/1984 | Itoh | 128/725 X |
| 4,495,944 | 1/1985 | Brisson et al. | 128/725 |
| 4,558,710 | 12/1985 | Eichler | 128/725 X |
| 4,711,585 | 12/1987 | Fresquez | 128/28 X |
| 4,739,987 | 4/1988 | Nicholson | 272/99 |
| 4,770,413 | 9/1988 | Green | 272/99 |

FOREIGN PATENT DOCUMENTS 350068 4/1974 United Kingdom ................. 272/99

Primary Examiner—Richard J. Apley
Assistant Examiner—Joe H. Cheng
Attorney, Agent, or Firm—Edward S. Irons

[57] ABSTRACT

In accordance with the present invention, a breathing exercise training apparatus is provided for increasing the endurance of inspiratory muscles. This is accomplished by setting a target breathing frequency, target inhalation time and target inhalation pressure on a target generator, and then having the trainee breathe into a resistive breathing device that imposes a predetermined resistance to inhalation and communicates actual inhalation pressure to the target generator. The target generator includes structure for comparing the actual inhalation time and pressure with the target values and provides a feedback signal in response thereto. A preset time interval is provided within which the trainee must attain the target inhalation pressure after an inhalation cycle begins, or a "fault" signal is given to the trainee. Thus, the apparatus of the invention forces the trainee to exercise his inspiratory muscles in order to achieve the target inhalation pressure within the target time.

8 Claims, 3 Drawing Sheets

RESPIRATORY TRAINING USING FEEDBACK

BACKGROUND OF THE INVENTION

A. Field of the Invention

The invention here relates to improving respiratory function of patients suffering from lung disorders through a program of breathing exercises. In particular, the invention relates to a method which provides feedback signals to a patient performing breathing exercises so that during the exercises target pressures for drawing air into the lungs and target rates for breathing are both achieved.

B. Description of the Prior Art

Breathing exercises have previously been prescribed to increase the inspiratory muscular endurance of persons having chronic obstructive pulmonary diseases such as chronic bronchitic emphysema, breathing problems caused by chest wall or muscle disease, or any condition requiring increased inspiratory muscular endurance. These previous exercises have included use of resistive training devices which are held in the mouth of a person doing breathing exercises while passage of air through the nose is blocked by a clip. The resistive training device restricts the flow of air into the lungs by including an orifice with a small cross-sectional area through which air must pass when the person inhales. When the person exhales, a one way valve, closed during inhalation, is open to facilitate unhampered passage of air The restriction of air flow is adjustable in these previous resistive training devices. During a set period of time each day a person exercising with the resistive training device breathes through the device, with the restriction to air flow set at a fixed value. Depending on the improvement of inspiratory muscle endurance, as measured by the onset of stress, e.g., tiring, shortness of breath, increased pulse rate and the like, the restriction to air flow through the training device can be increased so that the person using the training device must increase the use of the inspiratory muscles in order to breathe. A previously known training device which functions as discussed above, is described in U.S. Pat. No. 4,533,137 which issued Aug. 6, 1985 to Leonard J. Sonne.

SUMMARY OF THE INVENTION

The use of resistive training devices which have adjustable restrictions for controlling the flow of air that is inhaled may not effectively increase inspiratory muscle endurance. The job which the inspiratory muscles must achieve is filling the lungs with air. If a restriction to air flow smaller than the glottis, i.e., a hole about one half inch in diameter, is included in the passage to the lungs, by for example, a resistive training device, the inspiratory muscles can still fill the lungs with air but to do so these muscles may not have to work harder than if there is no restriction. For example, with a restriction in the passage to the lungs, the inspiratory muscles can fill the lungs by taking air in at a slower rate and over a longer period of time. Simply by stretching out the time air is drawn into the lungs and not increasing the pressure over that normally used to draw air into the lungs, the inspiratory muscles will not effectively be worked to increase endurance even though a resistive training device is being used. It is the product of the pressure differential between the air in the lungs and the air being drawn in by a person, times the volume of air which is drawn in that determines amount of work the inspiratory muscles perform. The prior training devices by only providing selection of different size restrictions to the passage of air could not be used for breathing exercises to increase inspiratory muscle endurance if the person using the device did not breath through the device so that the product of the pressure differential between the air in the lungs and the air being drawn in through the device times the volume of air being drawn in was not above that which the person obtained from normal breathing. By merely providing a person with a resistive training device having adjustable holes for setting resistance to air flow that person will initially set different goals from those of other persons and over time will not even maintain the initial goals for working the inspiratory muscles.

The present invention overcomes these differences in the prior resistive training devices and methods by providing a set of feedback signals to a trainee. These feedback signals provide a trainee with indications the trainee can use to assure that during each inhale, air is brought into the lungs at a minimum pressure differential and for a fixed period of time. By requiring a trainee to reach a minimum target pressure in drawing air through a fixed size restrictive hole and by fixing the period of time the trainee draws in air during each breath, the present invention provides a method which assures the inspiratory muscles are effectively worked to build endurance.

Apparatus for practicing the present invention includes resistive training device and a target generator. The resistive training device is held in the mouth of the trainee, while the noise is closed with a clip, so the trainee can breath air in and out through the resistive training device. Passage of air out of the resistive training device is unobstructed using a one way valve, whereas passage of air into the resistive training device is controlled by a narrowed orifice between the ends where air is brought into the resistive training device and into the trainee's mouth. The orifice for the present invention does not have to be adjustable in size; because it has been found that instead of decreasing the size of the orifice, to increase inspiratory endurance, the minimum pressure a trainee should attain in breathing through the resistive training device needs to be increased. The orifice must have a smaller cross-sectional area than that of the trainee's glottis. Further, the orifice needs to pass air flow rates to the trainee which do not significantly affect the percentage of carbon dioxide in the blood stream irrespective of changes in pressure targets, as will be explained below.

A pressure monitor system is positioned between the mouthpiece on the resistive training device and the orifice restricting flow of air. The pressure monitor system can be either a pressure transducer, such as a strain gauge transducer for sending signals to the target generator, or can be flexible tubing connected to the resistive training device which allows a pressure transducer to be located, for example, in the target generator. The target generator, in addition to monitoring the pressure the trainee develops when inhaling, also provides training feedback signals to the trainee. Lights, buzzers and meters can be used on the target generator to provide the feedback signals.

The feedback signals which the trainee must have in order to effectively work the inspiratory muscles and thus increase endurance are: (1) a signal to begin inhaling; (2) a signal to stimulate increased effort must be provided if within a fixed period of time the pressure which the trainee has developed does not exceed a target threshold; (3) a signal to warn the trainee if the target threshold for pressure has been excessively exceeded; (4) a signal to cease inhaling and begin exhaling; and (5) a signal to again begin inhaling.

Use of these feedback signals of the present invention regulate the trainee's breathing frequency, inspiratory time and inhalation pressure. By so regulating breathing exercises using a resistive training device the inspiratory muscles can be effectively worked and endurance developed.

BRIEF DESCRIPTION OF THE DRAWINGS

The present invention is configured so as to be portable and conveniently used by a trainee in every day situations, such as watching television, so that breathing exercises can be facilitated.

The novel features of the invention will be more readily appreciated from the following description when read in conjunction with the appended drawings, in which corresponding components are designated by the same reference numerals throughout the various figures.

DETAILED DESCRIPTION OF THE INVENTION

Figure 1:
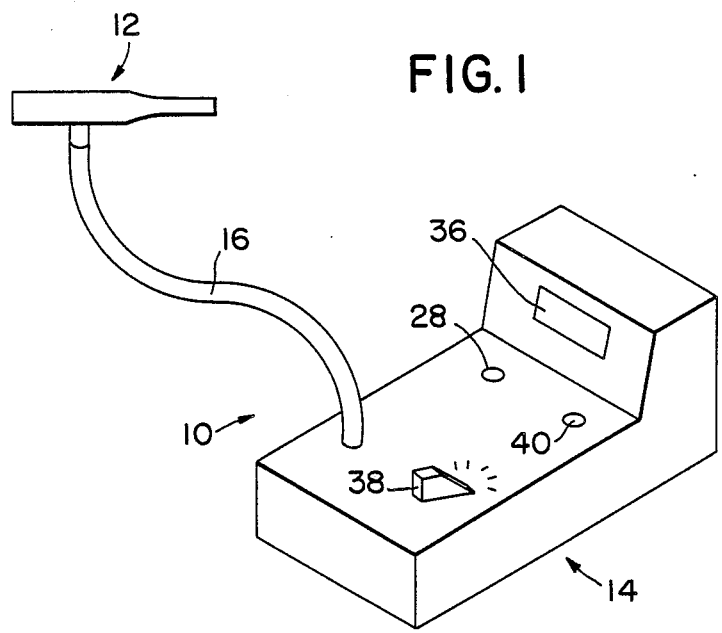
FIG. 1 is a perspective view of the respiratory training apparatus of the present invention including a resistive training device and target generator.
Figure 2:
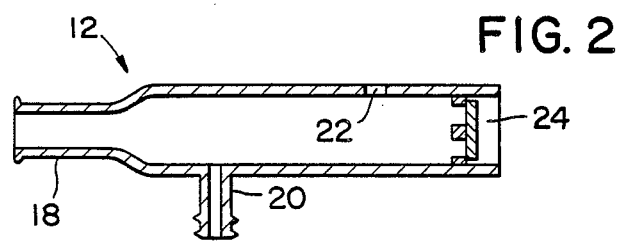
FIG. 2 is a sectional view of a resistive training device.

A respiratory training apparatus according to the present invention is shown in FIG. 1 where it is generally designated by reference to numeral 10. The respiratory training apparatus 10 includes a resistive training device 12 and a target generator 14. Connecting the resistive training device 12 to the target generator 14 is a pressure transfer tube 16.

The resistive training device 12 includes a mouthpiece 18, a pressure monitoring port 20, an air restriction orifice 22 and a one way valve 24. During breathing exercises the trainee holds the resistive training device 12 by the mouthpiece 18 in his mouth and breathes only through the resistive training device 12. When inhaling, air is brought into the resistive training device 12 through the orifice 22 because the one way valve 24 closes. On exhaling, air is passed through both the orifice 22 and the one way valve 24 which is then opened. It has been found that varying the size of the orifice 22 may not aid in developing inspiratory muscle endurance. Instead, by using the method of the present invention and an orifice 22 with a constant cross-sectional area of 0.17 square centimeters for passage of air, useful levels of inspiratory muscle work can be achieved. Further, this cross-sectional area for the orifice 22 allows trainees to breath through the resistive training device 12 without significantly changing the percentage of carbon dioxide in the blood stream irrespective of the level of inspiratory muscle work used to breath.

An acceptable resistive training device 12 for use in the respiratory training apparatus 10 is sold by Health-Scan Products, Inc. of Cedar Grove, N.J. under the trademark PFLEX. The PFLEX inspiratory muscle trainer includes a dial selector for setting different orifice sizes to restrict the flow of air during inhalation. The diameters of the different orifices on the PFLEX trainer are 0.54 centimeters, 0.46 centimeters, 0.40 centimeters, 0.30 centimeters, 0.22 centimeters and 0.17 centimeters. When used with the present invention it has been found useful to always set the dial selector to the hole size marked "2", which has a 0.46 centimeter diameter. This setting provides adequate air restriction and also does not cause the carbon dioxide level in the blood stream to significantly change during breathing exercises. A pressure monitoring port is included in PFLEX inspiratory muscle trainees and can be used to connect a Pressure transfer tube 16 to the target generator 14.

Figure 3:
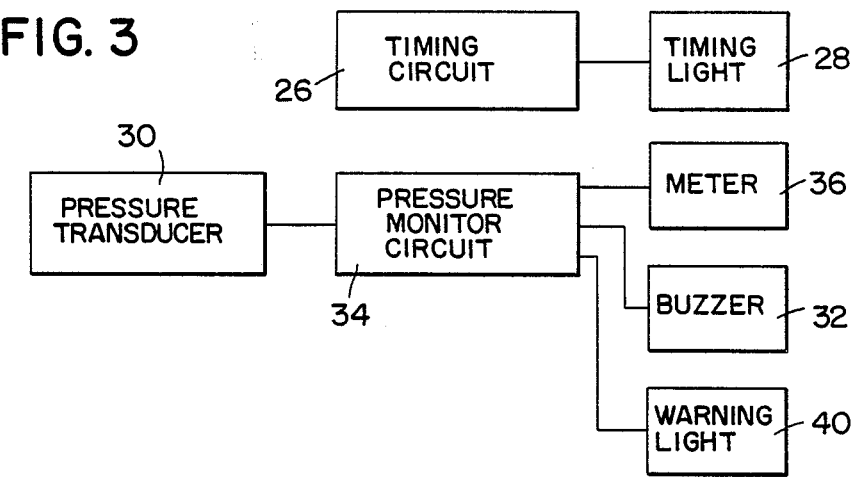
FIG. 3 is a block diagram of signal processor for a target generator of the present invention.

The target generator 14 includes a circuit which is shown in a block diagram in FIG. 3. Feedback signals to regulate breathing are provided to the trainee by the target generator 14. These feedback signals for the embodiment described here are a combination of visual and audio signals. The selection of whether the signals are visual or audio is a matter of choice. What is critical is that the trainee be given feedback signals to use for regulating breathing frequency, inspiratory time and inhalation pressure.

During breathing exercises a timing circuit 26 in the target generator 14 sends a signal to turn on a timing light 28. When the timing light 28 is turned on, the trainee begins to inhale air through the resistive training device 12. Within 0.4 seconds after the timing light 28 is turned on, the trainee must have created a target pressure in his mouth for inhaling air. To determine that the target pressure is reached, a pressure transducer 30, such as a pressure strain guage in the target generator 14, monitors the pressure in the trainee's mouth via the resistive training device 12 and the pressure transfer tube 16. If by that time the target pressure is not reached, a buzzer 32 is activated by a pressure monitor circuit 34. Also aiding the trainee with feedback information regarding the pressure developed by the respiratory muscles is a meter 36, receiving an analog signal representative of the magnitude of pressure from the pressure monitor circuit 34. The meter 36, by its needle provides the trainee with a linear indication of the magnitude of pressure being generated by the inspiratory muscles. In particular, the scale on the meter identifies the target pressure and whether that pressure is above or below the pressure being generated and by how much.

The target pressure is a variable which the trainee can select by turning a selector knob 38 on the target generator 14. The selector knob 38 is a twelve position rotary switch which sets target pressures from a low of 5 centimeters of water to a a high of 35 centimeters of water in 2.5 centimeters of water increments. As the trainee's inspiratory muscle endurance increases, he selects higher target pressures to increase endurance.

To protect the trainee from over exertion by having created too high a pressure, the pressure monitor circuit 34 using the pressure transducer 30 sends a signal to turn on a warning light 40 if the trainee generates a pressure of 50% more than the target pressure.

After 2.1 seconds from the time the timing light 28 is turned on, it is then turned off by the timing circuit 26. At that point, the trainee stops inhaling and begins exhaling for 2.7 seconds. Then the timing circuit 26 again turns on the timing light 28 and the series of steps described above are repeated. The rate of breathing this pattern provides is twelve and a half breaths per minute which is a normal breathing rate.

Using three normal subjects and five patients with severe chronic obstructive pulmonary disease the present invention was tested. The five choronic obstructive pulmonary disease patients had adequate blood oxygen tensions and had normal to mild hypercapnia (mean partial pressure of oxygen in arterial blood is 66 mm Hg, and mean partial pressure of carbon dioxide in arterial blood is 43 mm Hg).

All of the participants used resistive training devices sold under the trademark PFLEX and target generators in accordance with the above description of the present invention. The target generators provided inhalation feedback signals for 2.13 seconds using lighted green lamps, and adjustable target pressures between 5 centimeters of water increments. If after 0.4 seconds from the beginning of the inhalation feedback signal the selected pressure was not achieved, buzzers were sounded, and if the selected target pressure was exceeded by more than 20 percent red lights were turned on.

When the 21.3 second period for inhalation was over, the green lights were turned off 2.7 seconds, during which period the participants exhaled.

It was found that all of the participants, both normal subjects and breathing disorder patients, were able to follow the timing and pressure targets after short practice sessions of two to three preliminary runs of four minutes each. Their mean coefficient of variation for achieving the pressure target was 11% and the mean coefficient of variation for following the timing targets was 6%.

Figure 4:
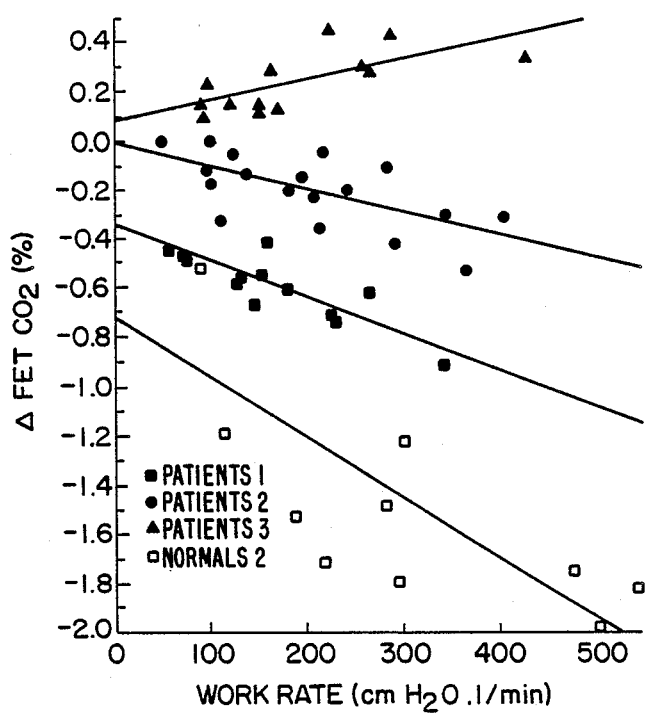
FIG. 4 is a graph of the change in carbon dioxide in the blood of normal subjects and breathing disorder patients versus work rate.

Various restriction orifice sizes were tested for the PFLEX resistive training device. Results of these tests include those shown in FIG. 4 where the percent change in carbon dioxide in the blood is shown on the vertical axis and the work rate for breathing is shown or the horizantal axis. The work rate is the pressure developed by the trainee's respiratory muscles times the rate a given volume of air is inhaled. Shown in FIG. 4 is the fact that normal subjects breathing through an orifice of 0.46 centimeter diameter (Lab number 2 on the PFLEX device) experience a decrease in the carbon dioxide in the blood as work rate is increased. Breathing disorder patients experience increased and decreased concentrations of carbon dioxide when breathing through orifices of 0.54 and 0.40 centimeter diameter (Labs number 1 and 2) respectively, when lab work rate is increased. Therefore, based on this data it is seen that for breathing disorder patients a restrictive orifice of 0.46 centimeter diameter (both number 2) provides adjustable target pressures in the range of from about 5 centimeters of water to about 35 centimeters of water, in 2.5 centimeter concentration in the blood over s range of work rates.

Figure 5:
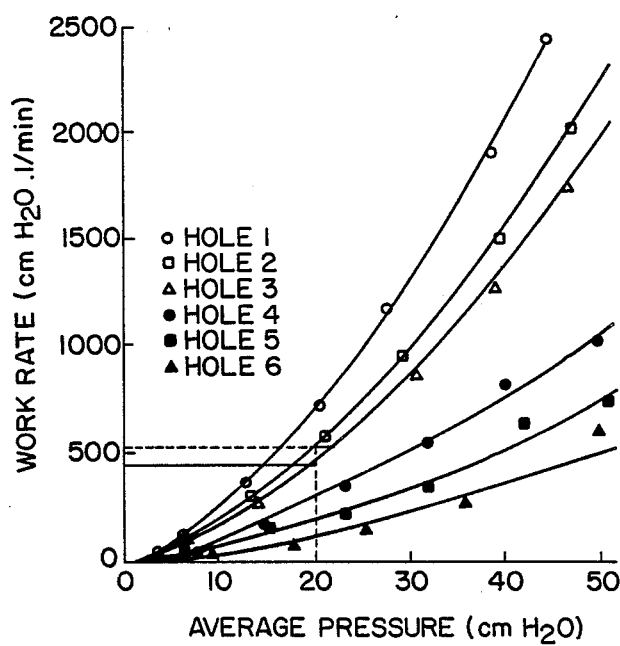
FIG. 5 is a graph of work rate versus pressure for the six hole sizes in PFLEX resistive device.

The relationship between restriction orifice diameter, work rate and pressure is shown in FIG. 5. As would be anticipated, increasing the pressure produced by inspiratory muscles does increase work rate. However, the rate of increase in work rates is highest for the largest diameter orifice (Lab 1) and lowest for the smallest diameter orifice (Lab 6). Beyond this qualitative conclusion it is seen that for a fixed pressure, e.g., 20 centimeters of water, breathing through hole number 1 produces a higher work rate than breathing through smaller orifices. The data presented in FIG. 5 was obtained using mechanical ventilation equipment. Using Labs 1, 2 and 3 on the PFLEX trainer the five breathing disorder patients produced the data set out on FIG. 6. This data shows that the conclusion from FIG. 5, namely large orifice sizes, can be more efficient for providing high work rates at given pressures than small orifice sizes, is correct for breathing disorder patients.

Figure 6:
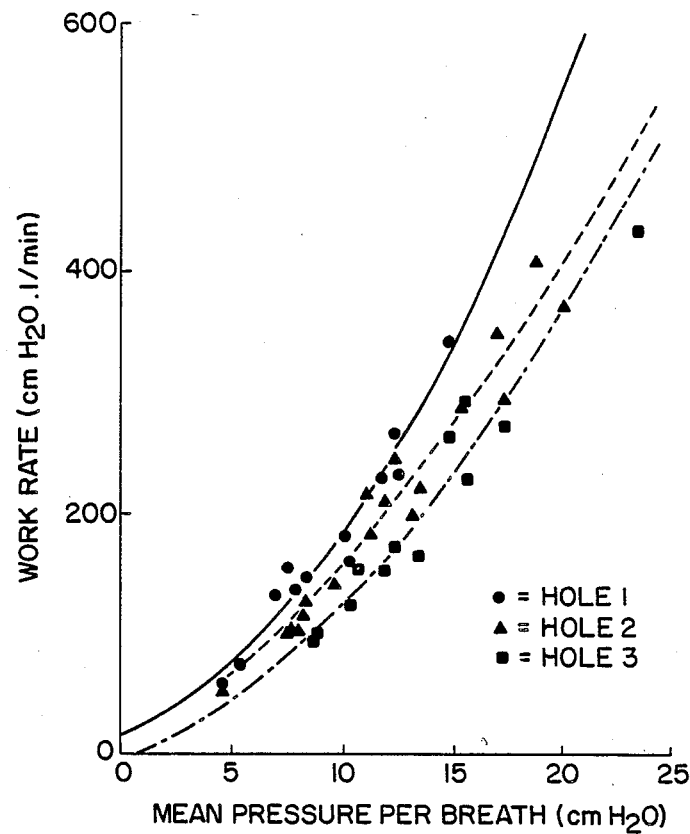
FIG. 6 is a graph of work rate versus pressure for three holes in the PFLEX resistive training device as produced by breathing disorder patients.

In conclusion, it is known that by increasing the amount of time air is inhaled, the work rate will decrease because the pressure has been decreased. From the data which is shown in FIGS. 5 and 6 this effect of decreasing work rate is seen to be in fact increased as orifice sizes decreases. Therefore, effective breathing exercises require that the time period for inhalation be fixed, the pressure to be fixed, and the orifice size by selected for an optimum rate of inhaling air. The optimum orifice size requires determination of the change in carbon dioxide in the blood as work rates are changed. For at least five breathing disorder patients an orifice diameter of 0.46 centimeters has been found appropriate. To provide for a fixed inhalation time and pressure during breathing exercises a target generator as described above has been found to be very effective.

The above discussion and related illustrations of the present invention are directed primarily to preferred embodiments and practices of this invention. However, it is believed that numerous changes and modifications in the actual implementation of the concepts described herein will be apparent to those skilled in the art, and it is contemplated that such changes and modifications may be made without departing from the scope of the invention as defined by the following claims.

What is claimed is:

1. A breathing exercise training apparatus for increasing the indurance of inspiratory muscles, comprising:

target generator means having timing means for setting and initiating a target timed interval for inhalation and a target timed interval for exhalation, and pressure responsive means for indicating a preselected target inhalation pressure and comparing it to actual inhalation pressure as attained by the trainee, said target generator means including signalling means for indicating when the target time intervals and the target inhalation pressure are not attained;

a resistive breathing device having a mouthpiece, an inlet orifice, an outlet opening and a pressure port connected with a pressure transducer in the target generator means for communicating to the target generator means the inhalation pressure attained by the trainee;

one-way valve means in said outlet opening for enabling flow out through said opening but preventing reverse flow inwardly therethrough;

said timing means in said target generator means producing a signal at the beginning of a timed target inhalation interval, which indicates to the trainee that he is to begin an inhalation cycle, and including signal means which provides a signal to the trainee if he has not attained the target inhalation pressure within a second preset time interval that is less than the timed target inhalation interval, whereby a trainee is taught to breath with a desired breathing frequency, inhalation time and inhalation pressure.

2. A breathing exercise training apparatus according to claim 1, in which said timed target inhalation interval is 2.1 seconds.

3. A breathing exercise training apparatus according to claim 1, in which said second preset time interval is generated by said timing means 0.4 seconds after said timed target interval for inhalation is begun.

4. A breathing exercise training apparatus according to claim 1, in which said target timed interval for exhalation is 2.7 seconds.

5. A breathing exercise training apparatus according to claim 1, in which said target generator means includes means for generating a feedback signal when the inhalation pressure attained by the trainee exceeds a preset high pressure threshold that is fifty percent higher than said preselected target pressure.

6. A breathing exercise training apparatus according to claim 1, in which said target generator means includes means for generating a feedback signal when the inhalation pressure attained by the trainee exceeds a preset high pressure threshold that is twenty percent higher than said preselected target pressure.

7. A breathing exercise training apparatus according to claim 1, in which said target inhalation pressure has a value in the range of from about 5 centimeters of water to about 40 centimeters of water.

8. A breathing exercise training apparatus according to claim 1 in which said resistive breathing means includes an adjustable restriction passage.

* * * * *